(12) United States Patent
Kondo et al.

(10) Patent No.: US 7,220,878 B2
(45) Date of Patent: *May 22, 2007

(54) METHOD OF PURIFYING AND SEPARATING 2-FLUORO-3-OXOALKYLCARBOXYLIC ACID ESTER

(75) Inventors: Norihisa Kondo, Yamaguchi (JP); Hideyuki Mimura, Yamaguchi (JP); Kosuke Kawada, Yamaguchi (JP); Shoji Arai, Yamaguchi (JP)

(73) Assignee: Tosoh F-Tech, Inc., Yamaguchi (JP)

( * ) Notice: Subject to any disclaimer, the term of this patent is extended or adjusted under 35 U.S.C. 154(b) by 499 days.

This patent is subject to a terminal disclaimer.

(21) Appl. No.: 10/490,432

(22) PCT Filed: Sep. 27, 2001

(86) PCT No.: PCT/JP01/08417

§ 371 (c)(1),
(2), (4) Date: Mar. 24, 2004

(87) PCT Pub. No.: WO03/031387

PCT Pub. Date: Apr. 17, 2003

(65) Prior Publication Data

US 2004/0249190 A1  Dec. 9, 2004

(51) Int. Cl.
*C07C 69/66* (2006.01)

(52) U.S. Cl. ............................ 560/184; 568/170
(58) Field of Classification Search ............. 560/184; 562/170

See application file for complete search history.

(56) References Cited

U.S. PATENT DOCUMENTS 6,020,502 A    2/2000  Chambers et al.
7,019,162 B2 *  3/2006  Kondo et al. ............... 560/184

FOREIGN PATENT DOCUMENTS

JP   2000-336064   12/2000
WO   95/14646      6/1995

* cited by examiner

*Primary Examiner*—Kamal A. Saeed
(74) *Attorney, Agent, or Firm*—Wenderoth, Lind & Ponack, L.L.P.

(57) ABSTRACT

The present invention concerns a method for purifying/separating a 2-fluoro-3-oxoalkylcarboxylic acid ester from a reaction mixture resulting from the fluorination of a 3-oxoalkylcarboxylic acid ester. The method involves depleting the reaction mixture of a hydrogen fluoride byproduct; and subsequently, separating the 2-fluoro-3-oxoalkylcarboxylic acid ester by distillation. The 2-fluoro-3-oxoalkylcarboxylic acid ester obtained by the method of the invention is highly pure and is thus suitable for use as an intermediate for the production of pharmacological products or agricultural chemicals.

13 Claims, No Drawings

METHOD OF PURIFYING AND SEPARATING 2-FLUORO-3-OXOALKYLCARBOXYLIC ACID ESTER

TECHNICAL FIELD

The present invention relates to a method for purifying/separating a 2-fluoro-3-oxoalkylcarboxylic acid ester, which is suitable for use as an intermediate for the production of pharmaceutical products and agricultural chemicals. Specifically, the method of the present invention allows the purification/separation of a 2-fluoro-3-oxoalkylcarboxylic acid ester by fluorinating a 3-oxoalkylcarboxylic acid ester, then depleting the reaction mixture of hydrogen fluoride, and subsequently separating the desired product from the reaction mixture by distillation.

BACKGROUND ART

Fluorine-containing dicarbonyl compounds, such as 2-fluoro-3-oxoalkylcarboxylic acid esters, are compounds of significant usefulness suitable for use as an intermediate for the production of pharmaceutical products and agricultural chemicals.

One way to produce these compounds is by directly fluorinating corresponding dicarbonyl compounds with fluorine gas. Examples of such techniques are described, for example, in J. Org. Chem. 57(1992): 2196, International Patent Publication Nos. WO 94/10120 and WO 95/14646, and Japanese Patent Laid-Open Publication No. Hei 09-255611. In each of these techniques, the goal is to selectively obtain a desired fluorine-containing dicarbonyl compound, such as the 2-fluoro-3-oxoalkylcarboxylic acid ester, and each technique involves directly fluorinating corresponding dicarbonyl compounds with fluorine gas.

However, the direct fluorination of a dicarbonyl compound with fluorine gas is a process involving free radicals and it is therefore difficult to selectively obtain only desired fluorine-containing dicarbonyl compound, such as the 2-fluoro-3-oxoalkylcarboxylic acid ester. For instance, the fluorination reaction described in the cited articles results in the generation of mono-fluoro forms, di-fluoro forms, and compounds containing more fluorine atoms.

In each of the techniques described in the cited articles, water is added to the reaction mixture after the fluorination reaction and the mixture is then extracted with dichloromethane. Nevertheless, none of the cited articles specifically describe any technique for purifying/separating a desired fluorine-containing dicarbonyl compound, such as the 2-fluoro-3-oxoalkylcarboxylic acid ester.

Using a known distillation technique, the present inventors have previously made attempts to separate the desired product from the reaction mixture, only to learn that the purification was difficult since the 3-oxoalkylcarboxylic acid esters, once fluorinated, readily degrade. Thus, there has been no choice other than to directly use the fluorinated 3-oxoalkylcarboxylic acid esters in the subsequent processes without distilling/purifying the reaction mixture. In a technique disclosed in European Patent No. 0440372A1, for example, a 2-fluoro-3-oxoalkylcarboxylic acid ester is reacted with amidine to produce a triazole derivative, a known fungicide. When this 2-fluoro-3-oxoalkylcarboxylic acid ester contains significant amounts of impurities, the purity of the reaction product is lowered and the generation of compounds of unknown structure is likely to result. Also, the low purity material significantly limits the reaction conditions and thus makes the production process difficult.

DISCLOSURE OF THE INVENTION

Accordingly, it is an objective of the present invention to provide a method for purifying/separating, at a high purity, a 2-fluoro-3-oxoalkylcarboxylic acid ester from a reaction mixture resulting from the fluorination of a 3-oxoalkylcarboxylic acid ester. Such a 2-fluoro-3-oxoalkylcarboxylic acid ester is suitable for use as an intermediate for the production of pharmaceutical products and agricultural chemicals.

In consideration of the current state of the art, the present inventors conducted extensive studies and found that the reaction mixture resulting from the fluorination of a 3-oxoalkylcarboxylic acid ester contains hydrogen fluoride, a byproduct generated during the fluorination, and that a 2-fluoro-3-oxoalkylcarboxylic acid ester readily degrades when heated in the presence of hydrogen fluoride. These findings implied that the distillation/purification process of the reaction mixture can be stabilized and the desired 2-fluoro-3-oxoalkylcarboxylic acid ester could be obtained at a high purity if hydrogen fluoride can be removed from the reaction mixture. It is this implication that inspired the present inventors to devise the present invention.

Accordingly, the present invention concerns a method for purifying/separating a 2-fluoro-3-oxoalkylcarboxylic acid ester from a reaction mixture resulting from the fluorination of a 3-oxoalkylcarboxylic acid ester. The method comprises the steps of depleting the reaction mixture of a hydrogen fluoride byproduct; and subsequently, separating the 2-fluoro-3-oxoalkylcarboxylic acid ester by distillation.

BEST MODE FOR CARRYING OUT THE INVENTION

The present invention will now be described in detail.

In the present invention, 3-oxoalkylcarboxylic acid ester to serve as a starting material is a β-dicarbonyl compound having an active methylene group. The alkyl of the 3-oxoalkylcarboxylic acid ester may be either a straight-chained alkyl or a cycloalkyl. In other words, the 3-oxoalkylcarboxylic acid esters include straight-chained 3-oxoalkylcarboxylic acid esters, cyclohexanone carboxylic acid esters, and cyclopentanone carboxylic acid esters. Preferably, straight-chained 3-oxoalkylcarboxylic acid esters are used, examples being 3-oxobutyric acid esters and 3-oxo-pentanoic acid esters. The ester may be methyl ester, ethyl ester or other lower alkyl esters.

The purification/separation method of the present invention is intended to be applied to a reaction mixture that results when a 3-oxoalkylcarboxylic acid ester is fluorinated with fluorine gas. For example, a technique described in International Patent Publication No. WO 95/14646 employs a fluorine gas diluted with an inert gas such as nitrogen to directly fluorinating a 3-oxoalkylcarboxylic acid ester. The reaction mixture for use in the present invention can be prepared by fluorinating a 3-oxoalkylcarboxylic acid ester according to this technique. In one example, a 3-oxoalkylcarboxylic acid ester is placed in a reactor equipped with a stirrer and a thermometer. While the solution of 3-oxoalkylcarboxylic acid ester is being stirred, approximately 10% fluorine gas diluted with nitrogen is bubbled through the solution to carry out the reaction. The reaction completes within 5 to 40 hours at a temperature of 0 to 15° C. although the time required for the reaction may vary depending on the amount of the starting material and the rate at which the fluorine gas is supplied. During the reaction, hydrogen fluoride is generated in an amount equal to the amount of the reacted fluorine gas and remains dissolved in the reaction mixture.

A first step of the present invention is to deplete the reaction mixture obtained through the fluorination of 3-oxoalkylcarboxylic acid ester of the hydrogen fluoride byproduct.

Hydrogen fluoride may be removed from the reaction mixture by washing the mixture with water or by distilling the reaction mixture under reduced pressure.

The washing with water requires approximately 0.5 to 3 times as much water as the reaction mixture. During the washing, the reaction mixture is fully exposed to water so that hydrogen fluoride dissolved in the mixture can be extracted. The hydrogen fluoride extracted with water exists as hydrofluoric acid. The extraction is preferably performed at 5 to 40° C. though it may be performed at any suitable temperature. Preferably, the water extraction is repeated 2 to 6 times, though the number of repeats may depend on the amount of water used. The extraction repeated 3 or 4 times would generate good results. During the washing, a water-insoluble organic solvent may be used in conjunction with water. Such organic solvents include dichloromethane, chloroform, 1,2-dichloroethane, toluene, and xylene. When used, the organic solvent extracts the reaction mixture and facilitates the separation of hydrogen fluoride by water. After washing, the organic phase is distilled to remove the organic solvent and the desired 2-fluoro-3-oxoalkylcarboxylic acid ester is then separated by distillation.

The distillation is performed under a reduced pressure at a temperature of 50° C. or below, preferably 40° C. or below, and is carried out by gradually increasing the degree of vacuum from atmospheric pressure to approximately 4.00 kPa (30 torr). The degree of vacuum is varied depending on the amount of hydrogen fluoride. Though the distillation may be performed over any suitable length of time, it is typically performed over a time period of 3 to 15 hours.

Alternatively, the reaction mixture may be depleted of hydrogen fluoride by forming an azeotrope with a proper azeotropic agent and distilling the azeotrope. Among the compounds that can form an azeotrope with hydrogen fluoride are ethers, such as dimethyl ether, diethyl ether, and diisopropyl ether; fluorochlorohydrocarbons, such as trifluoroethylchloride, Freon 12, and Freon 22; and hydrocarbons, such as butane, and isobutane. These azeotropic agents may be directly added to the reaction mixture or they may be continuously bubbled through the mixture.

In addition to the above-described techniques, a basic compound may be added to facilitate the removal of hydrogen fluoride. Examples of such basic compounds are hydroxides, carbonates, and bicarbonates of alkali metals and alkaline earth metals.

While it is preferred to remove as much hydrogen fluoride as possible, the amount of hydrogen fluoride is typically reduced to an amount of 2.0 wt % or less, and preferably to an amount of 1.0 wt % or less, with respect to the reaction solution. If the reaction mixture containing more than 2.0 wt % of hydrogen fluoride is subjected to the subsequent distillation step, the purity and the yield of the resulting 2-fluoro-3-oxoalkylcarboxylic acid ester will be undesirably decreased.

A second step of the present invention is to distill the hydrogen fluoride-depleted reaction mixture to separate the desired 2-fluoro-3-oxoalkylcarboxylic acid ester.

The purification/distillation of 2-fluoro-3-oxoalkylcarboxylic acid ester is preferably done by distilling the reaction mixture under reduced pressure. The process is preferably performed under 4.00 kPa (30 torr) or lower pressure and at as low temperature as possible, preferably 125° C. or below. If the temperature exceeds 125° C., the 3-oxoalkylcarboxylic acid ester, as well as its fluorinated derivatives, may become unstable and may thus become susceptible to thermal degradation. In this manner, the desired 2-fluoro-3-oxoalkylcarboxylic acid ester can be obtained at a high purity.

The present invention will now be described in detail with reference to examples, which are provided by way of example only and are not intended to limit the scope of the invention in any way. The followings are the names of the compounds used in Reference Examples, Examples, and Comparative Examples described below and their corresponding abbreviations:

MOP: 3-oxopentanoic acid methyl ester
MFOP: 2-fluoro-3-oxopentanoic acid methyl ester

REFERENCE EXAMPLE 1

5.0 kg of MOP were placed in a 10 L stainless steel-reactor equipped with a thermometer and a stirrer. A fluorine gas, diluted with nitrogen to a concentration of 10%, was bubbled through the reactant to carry out the reaction. The reaction was allowed to proceed for 20 hours with the temperature maintained at 10° C. and was then terminated. This gave 7.4 kg of a reaction mixture. A portion of the mixture was taken for analysis. The results of the analysis indicated that the mixture contained 42.6 wt % MFOP and 19.4 wt % hydrogen fluoride.

EXAMPLE 1

To 1 kg of the reaction mixture obtained in Reference Example 1, 1 L water and 1 L chloroform were added and the mixture was agitated in a separating flask at room temperature. Subsequently, the mixture was allowed to stand and the chloroform phase was collected. Water was added again and the same procedures were repeated until the chloroform phase was water-washed 4 times in total.

The water-washed chloroform phase was transferred to a stainless helix-packed distillation column having a theoretical plate number of 12 and a batch distillation was carried out. The chloroform phase was heated to about 40 to 60° C. while small amounts of nitrogen was bubbled through it. Subsequently, the pressure of the system was reduced to 26.7 kPa (200 torr) to distill out chloroform. The residual solution remaining in a still weighed 633 g and contained 66.8 wt % MFOP. The amount of hydrogen fluoride in the residual solution was determined to be 0.08 wt % by alkalimetry.

Using the residual solution, a batch distillation was performed in the following manner: The temperature of the still was first adjusted to 103° C. and the degree of vacuum from atmospheric pressure to 2.67 kPa (20 torr). After 4 hours, the temperature was decreased to 87° C. and the degree of vacuum was shifted to 1.33 kPa (10 torr). The distillation was terminated after about 15 hours. As a result, the residual solution was separated into three fractions: an early fraction composed mainly of low-boiling point products; a main fraction composed mainly of MFOP; and a residual fraction composed mainly of high-boiling point products. Each fraction was analyzed by gas chromatography for the MFOP concentration.

The early fraction weighed 85 g and contained 12.4 wt % MFOP. The main fraction weighed 402 g and contained 97.1 wt % MFOP, proven to have a sufficient purity. The residual fraction on the other hand weighed 140 g and contained 9.6 wt % MFOP. Collectively, the mass balance of the MFOP amounted to 98%, indicating little of the product was degraded.

EXAMPLE 2

To 1 kg of the reaction mixture obtained in Reference Example 1, 1 L water was added and the mixture was agitated in a separating flask at room temperature. Subsequently, the mixture was allowed to stand and the organic phase was collected. Water was added again and the same procedures were repeated until the solution was water-washed 3 times. After washing, the reaction mixture weighed 527 g and contained 64.7 wt % MFOP. The amount of hydrogen fluoride in the reaction mixture was determined to be 0.12 wt %.

The reaction mixture was then distilled under reduced pressure in the same manner as in Example 1. The early fraction weighed 53 g and contained 14.1 wt % MFOP. The main fraction weighed 321 g and contained 96.8 wt % MFOP, proven to have a sufficient purity. The residual fraction on the other hand weighed 145 g and contained 10.7 wt % MFOP. Collectively, the mass balance of the MFOP amounted to 98%, indicating little of the product was degraded.

EXAMPLE 3

1 kg of the reaction mixture of Reference Example 1, containing 19 wt % of hydrogen fluoride, was placed in the same type of distillation column as that used in Example 1. The mixture was then distilled under reduced pressure to remove dissolved hydrogen fluoride. The distillation was performed over 10 hours by gradually decreasing the pressure from atmospheric pressure first to 26.7 kPa (200 torr) and then to 6.67 kPa (50 torr) with the temperature of the still being kept under 40° C. The amount of hydrogen fluoride in the residual solution was determined to be 0.13 wt % by alkalimetry.

Subsequently, the solution was distilled under reduced pressure in the same manner as in Example 1. The outcome of the distillation was comparable to that of Example 1: the purity of MFOP in the main fraction was 97% and MFOP was obtained in 98% mass balance, indicating little product degradation had occurred.

EXAMPLE 4

Distillation under reduced pressure was carried out in the same manner as in Example 1, except that the temperature of the still was maintained at 110° C. during distillation. The purity of MFOP was 96% and the product was obtained 95% yield, indicating little product degradation had occurred.

EXAMPLE 5

To 1 kg of the reaction mixture obtained in Reference Example 1, 500 mL water was added. The resulting mixture was washed with water in the same manner as in Example 2 but only once. After washing, the reaction mixture contained 1.8 wt % hydrogen fluoride. The reaction mixture was then distilled under reduced pressure in the same manner as in Example 1. The purity of MFOP in the main fraction was 92% and the product was obtained 85% mass balance, indicating that degradation had taken place to some extent.

COMPARATIVE EXAMPLE 1

1 kg of the reaction mixture of Reference Example 1, which contained 19 wt % hydrogen fluoride, was placed in the same type of distillation column as that used in Example 1. The mixture was then distilled under reduced pressure while the degree of vacuum was gradually increased and the still was heated to 105° C. Significant degradation began to be observed 4 hours after the distillation under reduced pressure had been started. Since it became difficult to maintain the vacuum pressure of 2.67 kPa (20 torr) any longer, the distillation was discontinued.

INDUSTRIAL APPLICABILITY 3-oxoalkylcarboxylic acid ester, when fluorinated, gives rise to a mixture of different fluorinated products. To date, such a mixture has been used without purification. The present invention has for the first time enabled the production of highly pure 2-fluoro-3-oxoalkylcarboxylic acid esters. This achievement not only permits improvement in the quality of pharmaceutical products derived from the 2-fluoro-3-oxoalkylcarboxylic acid esters but also allows significant cost reduction in the production of such products.

The invention claimed is:

1. A method for purifying/separating a 2-fluoro-3-oxoalkylcarboxylic acid ester from a reaction mixture resulting from the fluorination of a 3-oxoalkylcarboxylic acid ester, the method comprising the steps of:
   depleting the reaction mixture of a hydrogen fluoride byproduct; and
   subsequently, separating the 2-fluoro-3-oxoalkylcarboxylic acid ester by distillation.

2. The method according to claim 1, wherein the depleting step comprises distilling hydrogen fluoride from the reaction mixture under reduced pressure at 50° C. or below.

3. The method according to claim 1, wherein the depleting step comprises washing the reaction mixture with water.

4. The method according to claim 1, wherein the reaction mixture contains hydrogen fluoride in an amount not exceeding 2.0 wt % after the depleting step.

5. The method according to claim 1, wherein the 3-oxoalkylcarboxylic acid ester is a lower alkyl ester of 3-oxo-butyric acid or 3-oxo-pentanoic acid.

6. The method according to claim 3, wherein the depleting step comprises washing the reaction mixture with water in the presence of a water-insoluble organic solvent.

7. The method according to claim 2, wherein the reaction mixture contains hydrogen fluoride in an amount not exceeding 2.0 wt % after the depleting step.

8. The method according to claim 3, wherein the reaction mixture contains hydrogen fluoride in an amount not exceeding 2.0 wt % after the depleting step.

9. The method according to claim 2, wherein the 3-oxoalkylcarboxylic acid ester is a lower alkyl ester of 3-oxo-butyric acid or 3-oxo-pentanoic acid.

10. The method according to claim 3, wherein the 3-oxoalkylcarboxylic acid ester is a lower alkyl ester of 3-oxo-butyric acid or 3-oxo-pentanoic acid.

11. The method according to claim 4, wherein the 3-oxoalkylcarboxylic acid ester is a lower alkyl ester of 3-oxo-butyric acid or 3-oxo-pentanoic acid.

12. The method according to claim 7, wherein the 3-oxoalkylcarboxylic acid ester is a lower alkyl ester of 3-oxo-butyric acid or 3-oxo-pentanoic acid.

13. The method according to claim 8, wherein the 3-oxoalkylcarboxylic acid ester is a lower alkyl ester of 3-oxo-butyric acid or 3-oxo-pentanoic acid.

* * * * *